US005575991A

United States Patent [19]

Kischka et al.

[11] Patent Number: 5,575,991

[45] Date of Patent: Nov. 19, 1996

[54] HAIR TREATMENT COMPOSITION CONTAINING POLYVINYLPYRROLIDONE AND BETAINE AMPHOTERIC SURFACTANT

[75] Inventors: Karl-Heinz Kischka, Darmstadt; Dietrich Hoch, Pfungstadt-Eich; Jürgen Schmenger, Weiterstadt; Ernst Flemming, Heusenstamm, all of Germany

[73] Assignee: Wella Aktiengesellschaft, Darmstadt, Germany

[21] Appl. No.: 259,758

[22] Filed: Jun. 13, 1994

[30] Foreign Application Priority Data

Jul. 31, 1993 [DE] Germany .......................... 43 25 817.4

[51] Int. Cl.$^6$ .............................. A61K 7/09; A61K 7/11

[52] U.S. Cl. .................... 424/70.2; 424/70.5; 424/70.51; 424/70.15

[58] Field of Search ............................ 424/70.15, 78.24, 424/78.4

[56] References Cited

U.S. PATENT DOCUMENTS

| | | | |
|---|---|---|---|
| 4,526,781 | 7/1985 | Goldberg et al. | 514/556 |
| 4,818,523 | 4/1989 | Clarke et al. | 424/70.12 |
| 4,834,968 | 5/1989 | Bolich, Jr. | 424/47 |
| 4,886,660 | 12/1989 | Patel et al. | 424/70.13 |

*Primary Examiner*—Peter F. Kulkosky
*Attorney, Agent, or Firm*—Michael J. Striker

[57] ABSTRACT

The aqueous or aqueous-alcoholic hair treatment composition contains:

A) 0.1 to 10 percent by weight polyvinylpyrrolidone or polyvinylpyrrolidone-vinyl acetate-copolymer;

B) 0.1 to 9 percent by weight of at least one amphoteric surfactant, preferably a fatty acid amidoalkylbetaine or a fatty acid amidoalkylsulfobetaine;

C) 0.1 to 5 percent by weight of at least one cationic surfactant, advantageously cetyltrimethylammonium chloride or bromide; and D) 0.1 to 2.0 percent by weight of at least one organic acid, preferably tartaric acid, glyoxalic acid, lactic acid or formic acid.

10 Claims, No Drawings

HAIR TREATMENT COMPOSITION CONTAINING POLYVINYLPYRROLIDONE AND BETAINE AMPHOTERIC SURFACTANT

BACKGROUND OF THE INVENTION

The present invention relates to an aqueous or aqueous-alcoholic composition for treating hair, which contains a combination of polyvinylpyrrolidone and/or polyvinyl-pyrrolidone-vinylacetate-copolymer with an amphoteric surfactant, a cationic surfactant and an organic acid. It also relates to methods of using that composition.

The physical, chemical and morphological properties of hair are influenced negatively by many different kinds of actions. Thus the hair is severely stressed and damaged, by cosmetic treatments, such as repeated bleaching, permanent wave treatments and hair dyeing, and also frequent washing with deoiling surfactants, by climatic influences such as moisture and temperature differences or the intensive action of sunlight and by mechanical treatment, such as brushing, combing and rubbing, especially in the vicinity of the hair tips, while the hair in the vicinity of the roots has a healthy undamaged structure. The greatly differing hair structure of the hair roots and the hair tips is a significant problem during the permanent wave treatment of hair. When the waving effectiveness of the permanent shaping composition for the hair is adapted to compensate for the worn and damaged hair tips, one generally obtains only an unsatisfactory permanent shaping of the hair at the hair roots. When one, in contrast, adjusts the effectiveness of the permanent shaping composition, for the undamaged hair at the hair roots, the hair at the worn hair tips can be damaged so very badly that curliness is significantly reduced or the individual hairs can even be broken.

During the permanent shaping of the hair performed with keratin-reducing shaping agents generally one first washes and then moistens the hair rubbed with a hand towel with a portion of a permanent shaping composition, then divides it into strands, winds these strands individually on permanent wave curlers and subsequently moistens the hair with the remaining portion of the permanent shaping composition. After finishing the permanent shaping process the hair is rinsed with water, then fixed oxidatively, subsequently removed from the curlers, rinsed with fresh water and, if necessary, after-treated with a treatment preparation.

This process has however several disadvantages. This sort of permanent shaping method can cause injury to the hands of the beauty shop personnel performing the treatment (e.g. allergies or other skin conditions), since the hands can come into contact with the permanent shaping composition for a total time amounting to about 20 minutes required for the curling or waving process. Moreover the above-described method is not very safe for the hair, since hair softening due to moistening of the hair with the hair shaping composition can very easily lead to an overstretching of the hair during the curling process on the curlers and, as a result of that, to hair breaking and hair falling out.

Moreover the hair is most strongly stressed after a hair shaping treatment so that an after-treatment with a hair care composition is necessary to again impart to the hair a natural touch and look.

SUMMARY OF THE INVENTION

It is an object of the present invention to provide a composition for treatment of hair, which protects the hair, especially the hair tips, during the permanent shaping process and thus permits a uniform shaping of hair.

It is also an object of the present invention to provide a composition for treatment of hair, which protects the hair, especially the hair tips, and which has satisfactory luster giving properties without stressing the hair.

According to the invention, the hair treatment composition is an aqueous or aqueous-alcoholic composition containing:

A) 0.1 to 10 percent by weight polyvinylpyrrolidone and/or polyvinylpyrrolidone-vinyl acetate-copolymer, B) 0.1 to 9 percent by weight of at least one amphoteric surfactant, C) 0.1 to 5 percent by weight of at least one cationic surfactant, and D) 0.1 to 2.0 percent by weight of at least one organic acid.

This hair treatment composition achieves the objects of the invention in an outstanding manner.

In a preferred embodiment of the invention component (A) is advantageously contained in an amount of from 0.1 to 4 percent by weight. Suitable polyvinylpyrrolidones are, for example, marketed under the Trademark Luviskol® K 90 of BASF, Ludwigshafen, Germany and under the Trademark PVP/® K 90 of ISP, Surrey, Great Britain. Suitable polyvinylpyrrolidone-vinyl acetate-copolymers are, e.g., marketed under the Trademark Luviskol®-VA of BASF, Ludwigshafen, Germany. The polyvinylpyrrolidone-vinyl acetate-copolymer of the component (A) advantageously has a ratio of polyvinylpyrrolidone monomer to vinyl acetate monomer of 60 to 40 and, e.g., is marketed by BASF, Ludwigshafen, Germany, under the Trademark Luviskol®-VA 64.

The hair treatment composition according to the invention advantageously contains 0.1 to 4 percent by weight of at least one amphoteric surfactant as component (B).

Alkylbetaine, alkylaminobetaine, fatty acid amidoalkylbetaine and fatty acid amidoalkylsulfobetaine are all suitable for the amphoteric surfactant used as component (B).

The amphoteric surfactant is advantageously either fatty acid amidoalkylbetaines and/or fatty acid amidoalkylsulfobetaines.

Coconut oil fatty acid amidopropyl betaine is advantageously contained as component (B), which for example is marketed by Goldschmidt, Essen, Germany, under the Trademark Tego Betain® L7, and/or 3-(3-coconut oil fatty acid amidopropyl)dimethylammonium-2-hydroxypropane sulfonate, which, e.g., is marketed in the form of a 50 percent aqueous solution under the Trademark Rewoteric® AM-CAS of Rewo Chemische Werke GmbH, Steinau, Germany.

Component (C) is present in the hair treatment composition of the invention in an amount of 0.1 to 2 percent by weight in a preferred embodiment of the invention.

Examples of suitable cationic surfactant of component (C) of the invention include the chlorides or bromides of alkyldimethylbenzylammonium salts, alkyltrimethylammonium salts, e.g. cetyltrimethylammonium chloride or bromide, tetra-decyltrimethylammonium chloride or bromide, alkyldimethylhydroxyethylammonium chloride or bromide, the dialkyl-dimethylammonium chloride or bromide, and alkylpyridinium salts, especially lauryl or cetyl pyridinium chloride, alkylamidethyltrimethylammonium ether sulfate and compounds with cationic character such as amine oxides, e.g. alklymethylamine oxide or alklyaminoethyldimethylamine oxide.

Cetyltrimethylammonium chloride is preferred as component (C), which for example is marketed as a 26% by weight aqueous solution under the Trademark Dehyquart® A of Henkel KGaA, Düsseldorf, Germany, under the Trademark Genamin® CTAC of Hoechst AG, Frankfurt, Germany and in the form of a 50% by weight solution of isopropanol under the Trademark Arquad® 16–50 of Akzo Chemicals GmbH, Düren, Germany.

The component (D) is present in an amount of from 0.1 to 1 percent by weight in a preferred embodiment of the invention.

The at least one organic acid used as component (D) in the hair treatment composition according to the invention, advantageously can be selected from the group consisting of tartaric acid, glyoxalic acid, lactic acid and formic acid.

A preferred embodiment of the hair treatment composition according to the invention can also contain 0.01 to 1 percent by weight, especially 0.01 to 0.1 percent by weight, of a keratin hydrolyzate, which for example is marketed in the form of a 20 percent by weight aqueous solution under the Trademark Keratin Liquid® of Cosnaderm, Ladenburg, Germany and of Croda GmbH, Nettal, Germany under the Trademark Crotein® WKP.

The hair treatment composition according to the invention advantageously has a pH of 2.5 to 4.5.

The hair treatment composition according to the invention can advantageously also contain all those ingredients, which are commonly used in hair treatment compositions, for example, especially, foam synergistic agents, foam stabilizers, sequestering agents; natural products; pigments; perfume oils in an amount of from 0.5 to 5.0 percent by weight; turbidity producing agents, for example ethylene glycol distearate, in an amount of from about 0.5 to 5.0 percent by weight; pearlescence imparting agents, such as a mixture of fatty acid monoalkylolamide and ethyleneglycol distearate, in an amount of about 1.0 to 10.0 percent by weight; thickening agents, such as coconut oil fatty acid diethanol amide or hydroxyalkyl cellulose, in an amount of 0.5 to 10.0 percent by weight; buffer substances, such as sodium citrate or sodium phosphate, in an amount of 0.1 to 1.0 percent by weight; dyes, such as Fluorescein-sodium salt, Gelb ZN3 (C.I. 47 055), in an amount of 0.1 to 1.0 percent by weight; additional hair care substances, such as fatty acid esters, fatty alcohols, fatty acid glycerides, ethoxylated or propoxylated saturated fatty alcohols; natural, modified natural or synthetic polymers, such as shellac; cationic, anionic or nonionic cellulose derivates, Chitosan, cationic Chitin- or Chitosan derivatives or polymerizates of acrylic acid derivatives; care materials, such as, e.g., lanolin derivates, cholesterin and pantothenic acid, in an amount of 0.1 to 10 percent by weight; moreover physiologically compatible inorganic salts, such as, e.g., sodium chloride and sodium sulfate; as well as additional moisturizing agents; anti-scaling agents; cosmetic oils and waxes as well as preservative materials. The composition of the invention can contain the above ingredients in so far as those ingredients appear useful and appropriate and are compatible with the components of the invention.

The composition according to the invention advantageously has a water content of 60 to 98.5 percent by weight and can contain alcohols in an amount of from 0.5 to 20 percent by weight. The preferred alcohols can be lower alcohols having one to four carbon atoms conventionally used for cosmetic purposes such as isopropanol and ethanol.

The hair treatment composition according to the invention is advantageously in the form of a preparation which is not rinsed from the hair after it is applied.

The hair treatment composition according to the invention can be applied as a hair structure regenerator prior to water spraying, fountain spray, hot wave or prior to a permanent shaping treatment.

The hair treatment composition according to the invention has outstanding conditioning properties. This hair treatment composition imparts to the hair a beautiful luster without impairing the retention of the permanent wave by the hair. The combability and the feel of the hair are clearly improved by use of the hair treatment composition according to the invention.

The hair treatment composition according to the invention is advantageously used as a pre-treatment agent in a permanent shaping of hair, which that it is applied to the hair prior to setting the hair with curlers.

The embodiments of the hair treatment composition according to the invention used as a pre-treatment agent during permanent shaping of hair causes a uniform shaping of hair during the permanent wave process. The sensitive hair tips and structurally damaged hair are protected by use of the hair treatment composition as a pre-treatment means during permanent shaping of hair so that a careful and safe permanent shaping of hair is possible.

Particularly structurally damaged hair has porous regions preponderantly in the scale layer, but also in the fiber stem. These porous regions are neutralized by the hair treatment composition according to the invention, which advantageously demonstrably surrounds the damaged regions of the hair, so that the hair damaging action of the permanent wave solution can be avoided.

Also the closing of the scale layer (Cuticle) of the hair, particularly by component (D) of the composition according to the invention, is promoted so that the diffusion of the waving ingredients of the permanent wave solution in the hair is delayed.

The curling of the hair on the permanent wave curlers is considerably simplified by use of the hair treatment composition according to the invention as the permanent wave pre-treatment means. Furthermore the hair treatment composition according to the invention, causes, when it is applied prior to a permanent shaping of the hair, a clear improvement in the springiness and elasticity of the permanently shaped hair.

The hair shaping composition according to the invention is advantageously in the form of an aqueous or aqueous-alcoholic solution and can be sprayed using a propellant means or with the help of mechanically operated spraying devices.

If the hair treatment composition is sprayed with the help of propellant means, it is advantageously prepared with from 3 to 75 percent by weight of propellant means and is filled in a pressurized container.

For example lower alkanes, such as n-butane, i-butane and propane or also their mixtures with dimethylether, and also with propellant gases under pressure, such as $N_2$, $N_2O$, and $CO_2$ and mixtures thereof, can be used as propellant means.

"Mechanical spraying devices" means devices which permit the spraying of the hair treatment composition without use of a propellant. Suitable mechanical spraying devices include spray pumps or an elastic container provided with a spray valve, in which the cosmetic composition according to the invention is filled under pressure. The cosmetic composition of the invention issues from the elastic container continuously when the spray valve is opened and the container is stretched after filling of it with the cosmetic agent.

The present invention further relates to a method for permanent shaping of hair in which one pre-treats the hair with the hair treatment composition according to the invention prior to curling the hair or winding the hair on the permanent wave curlers. Then the hair is dried, moistened with fresh water, wound on the curlers, then treated with a hair shaping composition, allowed to act on the hair for a predetermined acting time, rinsed from the hair, then oxidatively after-treated, rinsed with water, subsequently set into a hair do and then dried.

The hair is washed first with a shampoo in the method according to the invention and, after that, rinsed with water. Subsequently an amount of the hair treatment composition according to the invention sufficient for the permanent shaping pre-treatment, advantageously about 10 to 20 g, of the hair treatment agent according to the invention is applied to the hand towel dried hair, advantageously to the hair tips. After a sufficient acting time, which depending on the hair properties amounts to about 5 to 15 minutes, the hair is dried. Then the hair is moistened with water, without however rinsing the permanent wave pre-treatment composition from the hair. The hair is divided in strands and wound on the permanent wave curlers. The diameter of the curlers amounts to about 5 to 35 millimeters. Subsequently the hair is treated with a quantity of the hair shaping composition sufficient for the permanent shaping of hair, advantageously about 60 to 90 g.

A preferred permanent shaping composition for use in the method according to the invention is an aqueous alkaline preparation with a pH of from 7 to 10 which contains a keratin-reducing mercapto compound, such as Cysteine, Cysteamine, N-acetyl-L-cysteine, mercaptocarboxylic acids, for example thioglycolic acid or thiolactic acid, or salts of mercaptocarboxylic acids, such as ammonium and guanidine salts of thioglycolic acid or thiolactic acid, in a concentration of from about 2 to 12 percent by weight.

The required alkalinity is adjusted by addition of ammonia, organic amines, ammonium and alkali metal carbonates or hydrogen carbonates.

The permanent shaping composition for use in the method according to the invention can also be an aqueous acidic preparation with a pH of from 4.5 to 7 which contains an effective sulfite or mercaptocarboxylic acid ester content.

In the former or first case sodium or ammonium sulfites or the salt of sulfurous acid with an organic amine, such as monoethanolamines and guanidine, are used in concentrations of about 2 to 12 percent by weight(calculated as $SO_2$). In the latter or last case thioglycolic acid monoglycol ester or thioglycolic acid monoglycerine ester is used in concentrations of 5 to 50 percent by weight (corresponding to a concentration of 2 to 16 percent by weight of free thioglycolic acid). The hair shaping composition for the permanent shaping of hair can also contain a mixture of the previously-mentioned keratin-reducing compounds.

After an acting time sufficient for the permanent shaping of hair, which, according to the hair properties, the pH values, the shaping effectiveness of the shaping agent and the application temperature, amounts to about 10 to 30 minutes, the hair is rinsed with water and subsequently oxidatively after-treated ("fixed"). The after-treatment composition is, according to the hair amount, applied in an amount of from about 50 to 100 g.

Any conventional after-treatment composition used previously for an oxidative after-treatment can be used for the oxidative after-treatment in the method according to the invention. For example, sodium bromate, potassium bromate, sodium perborate, urea peroxide and hydrogen peroxide can all be used as the active agent in the oxidative after-treatment composition.

The concentration of the oxidizing agent in the oxidative after-treatment composition depends on the differing application times (usually about 5 to 15 minutes) and the application temperatures. The concentration of the oxidizing agent in the aqueous oxidative after-treatment composition is from about 0.5 to 10 percent by weight.

Both the permanent shaping composition and the oxidative after-treatment composition can be in the form of an aqueous solution or emulsion and also in thickened form on an aqueous basis, particularly in the form of a cream, gel or paste. It is similarly possible to fill these compositions under pressure in an aerosol cans and to dispense the compositions from the aerosol cans.

Subsequently the curlers are removed. As the case requires, the curled hair can be subjected to an additional oxidative after-treatment. Then the hair is rinsed with water, is set and subsequently dried.

The above-described process according to the invention for the permanent shaping of hair allows a careful and uniform shaping from the hair roots to the hair tips. The hair so treated has an outstanding wet and dry combability, a pleasant feel and a pronounced luster in the dry state as well as a loose, springy and simultaneously permanent wave, particularly in the vicinity of the hair tips.

An additional feature of the present invention resides in a method for treatment of hair which does not involve the subsequent permanent shaping of hair comprising distributing from 10 to 20 g of the hair treatment composition according to the invention on the hand-towel dried hair, if necessary setting the hair and then drying the hair.

The hair treated with the hair treatment composition according to the invention in the above-described manner has an outstanding wet and dry combability, a pleasant feel and a pronounced luster in the dried state.

EXAMPLES

Example 1: Hair Treatment Composition

| | |
|---|---|
| 0.600 g | Polyvinylpyrrolidone |
| 0.400 g | 3-(3-coconut oil fatty acid amidopropyl)-dimethylammonium-2-hydroxypropane sulfonate |
| 0.250 g | Cetyltrimethylammonium chloride |
| 0.100 g | Keratin hydrolyzate (Keratin Liquid ® of Cosnaderm/Ladenburg, Germany) |
| 0.100 g | Glyoxalic acid |
| 0.250 g | isopropanol |
| 98.300 g | water |
| 100.00 g | |

Example 2: Hair Treatment Composition

| | |
|---|---|
| 2.000 g | Polyvinylpyrrolidone |
| 0.750 g | 3-(3-coconut oil fatty acid amidopropyl)-dimethylammonium-2-hydroxypropane sulfonate |
| 0.104 g | Cetyltrimethylammonium chloride |
| 0.200 g | Citric acid |
| 96.946 g | water |
| 100.00 g | |

Example 3: Hair Treatment Composition

| | |
|---|---|
| 3.200 g | Polyvinylpyrrolidone |
| 1.950 g | 3-(3-coconut oil fatty acid amidopropyl)-dimethylammonium-2-hydroxypropane sulfonate |
| 0.234 g | Cetyltrimethylammonium chloride |
| 0.500 g | Chamomile blood extract (Extrapon ® Chamomile Special 2/033021 of Dragoco, Hozminden, Germany) |
| 0.250 g | Citric acid |
| 93.866 g | water |
| 100.00 g | |

Example 4: Hair Treatment Composition

| | |
|---|---|
| 0.700 g | Polyvinylpyrrolidone |

-continued

| | |
|---|---|
| 0.900 g | 3-(3-coconut oil fatty acid amidopropyl)-dimethylammonium-2-hydroxypropane sulfonate |
| 0.550 g | Cetyltrimethylammonium chloride |
| 0.150 g | Keratin hydrolyzate (Keratin Liquid ® of Cosnaderm/Ladenburg) |
| 0.100 g | Citric acid |
| 0.001 g | Gelb ZN3 (C.I. 47 005) |
| 0.550 g | isopropanol |
| 97.059 g | water |
| 100.00 g | |

Example 5: Hair Treatment Composition

| | |
|---|---|
| 0.700 g | Polyvinyl pyrrolidone |
| 1.050 g | 3-(3-coconut oil fatty acid amidopropyl)-dimethylammonium-2-hydroxypropane sulfonate |
| 0.600 g | Cetyltrimethylammonium chloride |
| 0.450 g | Lactic acid |
| 97.200 g | water |
| 100.00 g | |

Example 6: Hair Treatment Composition

| | |
|---|---|
| 2.000 g | Polyvinyl pyrrolidone-vinyl acetate-copolymer |
| 0.750 g | 3-(3-coconut oil fatty acid amidopropyl)-dimethylammonium-2-hydroxypropane sulfonate |
| 0.104 g | Cetyltrimethylammonium chloride |
| 0.200 g | Citric acid |
| 96.946 g | water |
| 100.00 g | |

While the invention has been illustrated and described as embodied in a hair treatment composition and method of using it, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Hair treatment composition comprising:

A) from 0.1 to 10 percent by weight of a member selected from the group consisting of polyvinylpyrrolidone and polyvinylpyrrolidone-vinyl acetate-copolymer;

B) from 0.1 to 9 percent by weight of at least one amphoteric surfactant selected from the group consisting of fatty acid amidoalkylbetaines and fatty acidamidoalkylsulfobetaines;

C) from 0.1 to 5 percent by weight of at least one cationic surfactant;

D) from 0.1 to 2.0 percent by weight of at least one organic acid; and

E) water, so that said composition provides improved curl droop properties when applied to hair.

2. Hair treatment composition as defined in claim 1, containing from 0.1 to 4 percent by weight of said member.

3. Hair treatment composition as defined in claim 1, containing from 0.1 to 4 percent by weight of said at least one amphoteric surfactant.

4. Hair treatment composition as defined in claim 1, containing from 0.1 to 2 percent by weight of said at least one cationic surfactant.

5. Hair treatment composition as defined in claim 1, wherein said at least one cationic surfactant comprises cetyltrimethylammonium chloride.

6. Hair treatment composition as defined in claim 1, containing from 0.1 to 1 percent by weight of said at least one organic acid.

7. Hair treatment composition as defined in claim 1, wherein said at least one organic acid is selected from the group consisting of tartaric acid, glyoxalic acid, lactic acid and formic acid.

8. Hair treatment composition as defined in claim 1, further comprising from 0.01 to 1 percent by weight of keratin hydrolyzates.

9. Hair treatment composition as defined in claim 1, further comprising an alcoholic substance selected from the group consisting of alcohols having from 1 to 4 carbon atoms.

10. Hair treatment composition as defined in claim 1, wherein said at least one amphoteric surfactant comprises 3-(3-coconut oil fatty acid amidopropyl)-dimethylammonium-2-hydroxypropane sulfonate.

* * * * *